US005606041A

United States Patent [19]

Busch et al.

[11] Patent Number: 5,606,041

[45] Date of Patent: Feb. 25, 1997

[54] PROCESS FOR STEROIDAL PERACYL GLYCOSIDES

[75] Inventors: Frank R. Busch, Gales Ferry; Kathleen D. Goggin, Colchester; John F. Lambert, North Stonington; Russell J. Shine, Waterford; Stanley W. Walinsky, Mystic, all of Conn.

[73] Assignee: Pfizer Inc., New York, N.Y.

[21] Appl. No.: 351,472

[22] PCT Filed: Apr. 2, 1993

[86] PCT No.: PCT/US93/02812

§ 371 Date: Dec. 20, 1994

§ 102(e) Date: Dec. 20, 1994

[87] PCT Pub. No.: WO94/00479

PCT Pub. Date: Jan. 6, 1994

Related U.S. Application Data

[63] Continuation of Ser. No. 905,599, Jun. 26, 1992, abandoned.

[51] Int. Cl.[6] .................... C07G 3/00; C07H 15/00; C07J 9/00

[52] U.S. Cl. .................... 536/18.5; 536/5; 536/6; 536/6.1; 536/18.6

[58] Field of Search .................... 536/5, 6, 6.1, 18.5, 536/18.6; 514/26

[56] References Cited

U.S. PATENT DOCUMENTS

| | | | |
|---|---|---|---|
| 2,991,282 | 4/1961 | Rubin | 540/18 |
| 3,303,187 | 2/1967 | Rubin | 540/18 |
| 3,935,194 | 1/1976 | Loken | 260/239.55 |
| 3,981,867 | 9/1976 | Beauvoir | 540/18 |
| 4,254,111 | 3/1981 | Pegel et al. | 536/5 |
| 4,260,603 | 4/1981 | Pegel et al. | 514/26 |
| 4,562,250 | 12/1985 | Staba et al. | 536/6.1 |
| 4,602,003 | 7/1986 | Malinow | 514/26 |
| 4,602,005 | 7/1986 | Malinow | 514/26 |
| 4,675,392 | 6/1987 | Dahmen et al. | 536/17.9 |
| 5,010,185 | 4/1991 | Urban | 536/6.1 |

FOREIGN PATENT DOCUMENTS

| | | |
|---|---|---|
| 0159431 | 10/1985 | European Pat. Off. . |
| 0403150 | 12/1990 | European Pat. Off. . |
| 2523284 | 12/1976 | Germany . |
| 2024624 | 1/1980 | United Kingdom . |
| 9311150 | 11/1991 | WIPO . |

OTHER PUBLICATIONS

*Carbohydrate Chemistry,* Ed. Hassan S. El-Khadem, Published by Academic Press, Inc., pp. 179–180, (1988).

Nishizawa et al. *Synlett,* vol. 10, pp. 797–799, (1992) [Abstract Only].

Kintya et al. *Khim. Farm. Zh.*, vol. 15(9), pp. 55–60, (1981).

Freire et al. *Chromatography in Biochemistry, Medicine and Environmental Research,* vol. 1, pp. 249–259, (1983).

Nishizawa et al. *Chem. Pharm. Bull.* 41(4), pp. 784–785, (Apr. 1993).

Higashi et al. *Chem. Pharm. Bull.* 40(4), pp. 1042–1043, (1992).

Higashi et al. *Chem. Pharm. Bull.*, vol. 40(8), pp. 2019–2022, (1992).

Caglioti et al., Tetrahedron 19, 1127–1131 (1963).

K. Freudenberg and W. Nagari, Ann., 494,63 (1932).

Malinow et al., Steroids, vol. 48, pp. 197–211 (1986).

Marker et al., J. Amer. Chem. Soc., 69, 2167–2211 (1947).

Schmidt, Angew. Chem. Int. Ed. Engl., vol. 25, pp. 212–235 (1986).

Urban et al., Synthesis of Tigogen (β–O–Cellobioside Heptacetate and Glycoside Tetraacetate via Schmidt's Trichloroacetimidate Method, Some New Observations, Tetrahedron Letters, vol. 31, pp. 4421–4424 (1990).

Hashimoto et al., Glycosylation Using Glucopyranosyl Fluorides and Silicon–Based Catalysts, Tetrahedron Letters, vol. 25, No. 13, pp. 1379–1382 (1984).

Nishizawa et al., Total Synthesis of Cyclo–L–Cyclo–L–Rhamnohexase by a Stereoselective Thermal Glycosylation, Tetrahedron Letters, vol. 32, No. 40, 5551, (1991).

R. Mietchen et al., Reactions with and in Anhydrous Hydrogen Fluoride[1]. Selective Systems of Glycosyl Fluorides. Z. Chem. vol. 30, 2, pp. 55–67 (1990) (Translation provided).

Nishizawa et al., Thermal Glycosidation with Benzylated Glycosyl Chlorides: A Very Simple Procedure for O–Glycosidation, Chem. Pharm. Bull., 37(2), 565 (1989).

R. Nyori et al., Chem. Abstracts, 104, 19, p. 703, No. 168762 (1986).

J. E. Oliver et al., "Glucosylations of Pregn–5–ene–3–beta, 2OR–diol", Steroids: Structure, Function, and Regulation, 52, 3, pp. 265–278 (1988).

H. Kunz et al., "Stereoselective Glycosylation of Alcohols and Silyl Ethers Using Glycosyl Fluorides and Boron Trifluoride Etherate", Helvetica Chimica Acta, 68, 1, pp. 283–287, (1985).

*Primary Examiner*—Gary E. Hollinden
*Assistant Examiner*—Howard C. Lee
*Attorney, Agent, or Firm*—Peter C. Richardson; Gregg C. Benson; A. Dean Olson

[57] ABSTRACT

Processes for the synthesis of tigogenin beta-O-cellobioside heptaalkanoate which is an intermediate for the known hypo-cholesterolemic agent tigogenin beta-cellobioside. The process comprises reacting α-cellobiosyl bromide heptaalkanoate and β-tigogenin in the presence of zinc fluoride or zinc cyanide under conditions capable of forming said tigogenyl β-O-cellobioside heptaalkanoate. The analogous preparations of hecogenin β-O-cellobioside heptaalkanoate 11-ketotigogenin β-O-cellobioside heptaalkanoate, and diosgenin β-O-cellobioside heptaalkanoate are also disclosed. The process provides both high β-anomeric selectivity and high yields.

10 Claims, No Drawings

PROCESS FOR STEROIDAL PERACYL GLYCOSIDES

This application was filed under 35 U.S.C. §371 based on PCT/US93/02812, which was filed on Apr. 2, 1993 which is a continuation of U.S. application Ser. No. 07/905,599 which was filed on Jun. 26, 1992 and is now abandoned.

BACKGROUND OF THE INVENTION

The present invention relates to processes for the synthesis of steroidal glycosides, and particularly to the preparation of steroidal peracyl glycosides used as intermediates therein.

Tigogenin beta-O-cellobioside is a known compound having utility in the treatment of hypercholesterolemia and atherosclerosis (Malinow, U.S. Pat. Nos. 4,602,003 and 4,602,005; Malinow et al., Steroids, vol. 48, pp. 197–211, 1986). Each patent discloses a different synthesis of this compound from alpha-D-cellobiose octaacetate; the first via the glycosyl bromide heptaacetate which is coupled with tigogenin in the presence of silver carbonate, and finally hydrolyzed; and the second via direct stannic chloride catalyzed coupling of the cellobiose octaacetate with tigogenin in methylene chloride, again followed by hydrolysis. In Malinow et al., reaction of cellobiose octaacetate with titanium tetrabromide gave the cellobiosyl bromide heptaacetate, which was coupled with tigogenin by means of mercuric cyanide, and then hydrolyzed. All of these methods have serious drawbacks for producing bulk material to be used as a pharmaceutical drug. A desirable goal, met by the present invention, has been to devise synthetic methods which avoid toxic and/or expensive reagents, and which cleanly produce the desired tigogenin beta-O-cellobioside, avoiding tedious and expensive purification steps.

Schmidt, Angew. Chem. Int. Ed. Engl., vol. 25, pp. 212–235 (1986) has reviewed the synthesis and reactions of O-glycosyl trichloroacetimidates formed by the reaction of sugars possessing a 1-hydroxy group (but with other hydroxy groups protected, e.g., by benzyl or acetyl) with trichloroacetonitrile in the presence of a base. There is preferential formation of the alpha-anomer when sodium hydride is used as base, and preferential formation of the beta-anomer when the base is potassium carbonate. The alpha anomer of tetrabenzylglucosyl trichloroacetimidate when coupled with cholesterol gave anomeric mixtures which varied with catalyst (p-toluenesulfonic acid or boron trifluoride etherate) and temperature (–40° to +20° C.). On the other hand, both the alpha and beta anomers of tetraacetylglucosyl analog reportedly yielded exclusively beta-anomeric products.

Thus, there has been a continuing search in this field of art for improved methods of stereocontrolled syntheses of steroidal glycosides. For example, Gilbert Stork, J. Am. Chem. Soc. 1992, 114, 1087 and the authors cited therein support the need for better stereoselective glycoside syntheses.

SUMMARY OF THE INVENTION

This invention is directed to a process for the synthesis of 1-O-steroidal-peracyl-β-glycosides that provides greater β-anomeric selectivity with reduced by-products and side reactions. The process comprises reacting heptaacyl-D-cellobiosyl-1-halide, tetraacyl-D-glucosyl-1-halide or tetraacyl-D-galactosyl-1-halide and a trisubstituted silyl-3-O-steroid, wherein the steroid is tigogenin, hecogenin, 11-ketotigogenin, diosgenin, or cholesterol, in the presence of zinc fluoride under suitable conditions. Typically, the halide is bromide, chloride or fluoride, the acyl is alkanoyl($C_1$-$C_6$), benzoyl or toluoyl and the silyl substitution is alkyl($C_1$-$C_6$), phenyl or phenyl alkyl($C_1$-$C_6$).

In a preferred aspect of this invention the metal salt is zinc fluoride, the acyl is acetate, the silyl substitution is methyl and the peracyl glycosyl halide is the α-anomer. In a particularly efficient, especially preferred process, substantially stoichiometric amounts of the glycosyl compounds and trimethylsilyl ethers of the steroids are reacted together. This is a significant advantage over earlier processes which used excess glycosyl halide.

Other features and advantages will be apparent from the specification and claims.

DETAILED DESCRIPTION OF THE INVENTION

The metal salt used in the stereospecific coupling of the silyl sterol ether and glycosyl compounds may be zinc fluoride, zinc bromide or zinc cyanide. It is especially preferred that the metal salt is zinc fluoride which is believed to work best when the zinc fluoride salt possesses a rhombic crystal morphology. It is preferred that about 0.1 equivalents (equivalents as used hereinafter means based on the glycosyl halide) to about 1.5 equivalents and especially preferred that about 0.2 equivalent to about 0.7 equivalent of the metal salt is used. The dependence of the glycosidic coupling on the $ZnF_2$ equivalents is described in Table 4 below. The zinc salts can also be used in combination with Lewis and mineral acids that are effective in providing faster reaction rates as described in Table 3 below. Particularly preferred acid catalysts include hydrobromic acid, hydrochloric acid, hydrofluoric acid and sulfuric acid. For faster reaction rates, it is preferred that about 0.05 equivalents to about 1 equivalents, and especially preferred that about 0.1 equivalent to about 0.5 equivalents acid catalyst is used. However, it is especially preferred that the glycosidic coupling is acid catalyzed and it is especially preferred that the hydrohalic acid generated during the reaction by vestigial water is used as the acid catalyst.

Preferably the peracyl-D-glycosyl-1-halides used to couple with the silyl sterol ether is heptaacyl-D-cellobiosyl-1-halide, tetraacyl-D-glucosyl-1-halide or tetraacyl-D-galactosyl-1-halide. As used herein the term peracyl refers to the substitution by an acyl group on each of the available hydroxy positions of the saccharidyl moiety. Although, the peracyl-D-glycosyl-1-halides can be the beta anomer it is preferred that the α-anomer is used. In addition, although the halide may be bromide, fluoride or chloride it is preferred that the halide is bromide. It is also preferred that the acyl is alkanoyl ($C_1$-$C_6$), benzoyl or toluoyl and especially preferred that the acyl is acetyl. They may be prepared from conventional starting materials according to methods described in K. Freudenberg and W. Nagai, Ann., 494, 63 (1932). It is especially preferred that a substantially stoichiometric quantity of peracyl-D-glycosyl-1-halide be used as this avoids using excess reagents while maintaining excellent stereospecificity and high reaction yields.

Any reaction inert solvent may be used. As used above and elsewhere herein, the expression "reaction-inert solvent" refers to a solvent which does not react or decompose with starting materials, reagents, intermediates or products in a manner which adversely affects the yield of the desired product. In general, the solvent can comprise a single entity, or contain multiple components. Preferably the solvent is a non-protic reaction inert solvent and it is especially preferred that the solvent is acetonitrile because of the excellent stereoselectivity it provides. Other solvents include methylene chloride, ethyl acetate and nitromethane.

Tigogenin's preparation is described by Rubin in U.S. Pat. Nos. 2,991,282 and 3,303,187, by B. Löken in U.S. Pat. No.

3,935,194 and Caglioti et al., Tetrahedron 19, 1127 (1963). It is a natural product which can be isolated from plants. Its structure is depicted below.

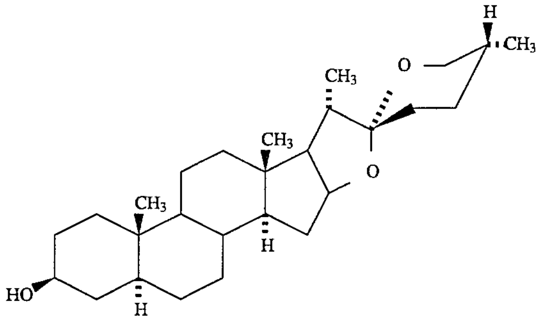

Hecogenin's preparation is described in a paper on Steroidal Sapogenins by Russell E. Marker et al., in J. Amer. Chem. Soc., 69, 2167–2211 (1947). It is a natural product which can be isolated from plants. Its structure is depicted below.

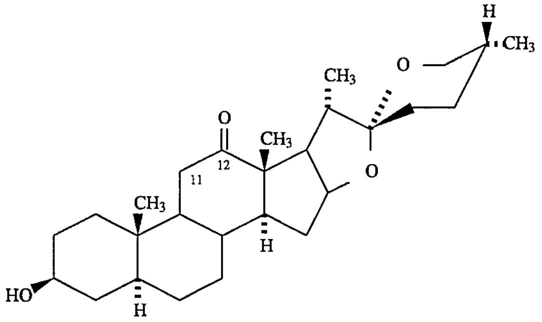

11-keto-β-tigogenin switches the carbonyl group from the 12 position to the 11 position of the structure depicted above. 11-keto-β-tigogenin's is prepared from hecogenin by the following procedure. According to the procedure of Conforth, et al., (J. Chem. Soc., 1954, 907), hecogenin is acetylated, brominated, treated with sodium hydroxide and reduced with zinc to give the 12-hydroxy-11-keto analog. Then 12-hydroxy-11-keto analog is acetylated and reduced with calcium and ammonia to give 11-keto-tigogenin.

Diosgenin's preparation is described in "Diosgenin and other Steroidal Drug Precursors" by Asolkar, L. V., Chadha, Y. R., and Rawat, P. S., Council of Scientific and Industrial Research, New Delhi, India, 183 pages, 1979 and also in T. Kawasaki et al., Chem, Pharm. Bull., Japan 10, 698 (1962). It is a natural product which can be isolated from plants. Its structure is depicted below.

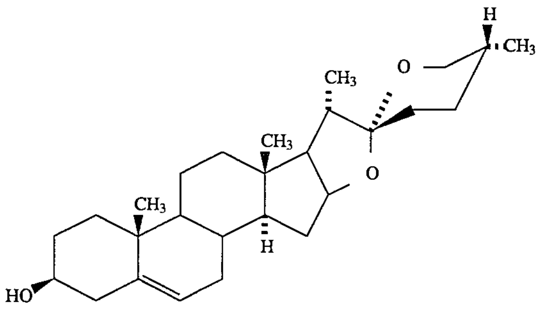

Cholesterol is a readily available compound, it's structure is depicted below.

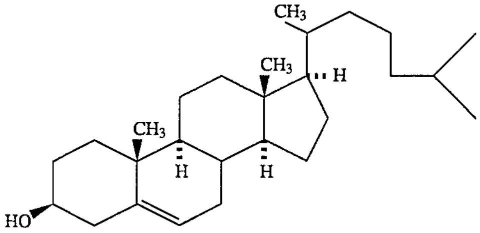

Although any trisubstituted silyl ether (3-hydroxy substitution) of the above steroids may be coupled with the peracyl glycosyl halides it is preferred that an alkyl ($C_1$-$C_6$) or aryl (i.e. phenyl, alkyl($C_1$-$C_6$)phenyl) trisubstituted silyl ether be used. It is especially preferred that a trialkyl ($C_1$-$C_6$) silyl ether be used, particularly trimethyl silyl ether, t-butyldimethyl silyl ether, triisopropyl silyl ether, phenyldimethyl silyl ether or triethyl silyl ether.

The above silyl ether steroids may be prepared by reacting a trisubstituted silyl trifluoromethanesulfonate with the appropriate steroid in the presence of a trialkylamine (e.g. triethylamine) at a temperature less than about 10° C. for about 0.5 to about 6 hours. Appropriate procedures may also be found in L. Birkofer and A. Rifler, "Newer Methods in Preparative Organic Chemistry," Vol. V. p. 211, Academic Press, New York, N.Y. 1968 or A. E. Pierce, "Silylation of Organic Compounds," Pierce Chemical Co., Rockford, Ill., 1968., and J. F. Klebe, Acc, Chem. Res., 1970 (3) 299.

Preferably about 0.5 equivalent to about 1.5 equivalents of the steroidal silyl ether is used in the coupling reaction. It is especially preferred that a substantially stoichiometric quantity of the steroidal silyl ether be used as this avoids using excess reagents while maintaining excellent stereospecificity.

Any environment or conditions (e.g., temperature, time, pressure, solvent,) suitable for (i.e., capable of) forming the desired steroidal peracyl glycosides may be used. However, it is preferred that the reaction occurs at a temperature of about 20° C. to about 100° C. and preferably from about 50° C. to about 80° C. Below about 20° C. the reaction can be slow and above about 100° C. undesired side reactions (e.g. anomerization) can occur. This reaction is conveniently carried out at ambient pressure, however, pressures from about 0.5 to about 3 atmospheres may be used.

Preferably the steroidal silyl ether, metal salt, solvent are heated to reflux and sufficient solvent is azeotropically distilled to remove substantially all the water. Then the peracyl glycosyl halide and optional acid catalyst is added to the above mixture and heated for about 0.5 to about 6.0 hours, typically under nitrogen. The desired compounds are then isolated by conventional methods. For example, the glycosides may be precipitated from the crude filtered reaction mixture (e.g. acetonitrile product solution) by the addition of about 25% to 75% water and the remainder alcohol (e.g. methanol). Precipitation of the product from aqueous methanol/acetonitrile requires less processing than an extractive isolation, and provides a product of greater purity. Alternatively, the steroidal silyl ether may be prepared, not isolated and directly coupled with the peracyl glycosyl halide.

Although the above process is designed to synthesize steroidal glycosides of the β configuration, the more thermodynamically stable α-anomers are accessible by acid-catalyzed isomerization of the β-glycosides. Therefore, peracyl steroidal α-O-glycosides can be prepared from peracyl steroidal β-O-glycosides by heating the β-glycosides in organic solvents such as a methylene chloride solution containing hydrogen bromide.

The zinc fluoride-mediated glycosidic coupling of TMS-O-tigogenin and α-cellobiosyl bromide heptaacetate was conducted in the presence of different reaction solvents at varying temperatures. The results of these solvent evaluations are summarized below in Table 1. This demonstrates that acetonitrile is a preferred solvent for stereocontrolled glycoside syntheses.

TABLE 1

$ZnF_2$-PROMOTED GLYCOSIDIC REACTIONS WITH TMS-O-TIGOGENIN INFLUENCE OF REACTION SOLVENTS
Reaction Stoichiometry:
α-Cellobiosyl Bromide Heptaacetate (1.0 Equivalent)
TMS-O-Tigogenin (1.0 Equivalent)
$ZnF_2$ (0.55 Equivalent)
Solvent

| | REACTION | | YIELD | |
|---|---|---|---|---|
| Solvent | Time | Temp. | β-Glycoside | α-Glycoside |
| $CH_3CN$ | 2.5 hrs. | 65° C. | 71% | 4% |
| DMF | 4.0 hrs. | 70° C. | 2% | 1% |
| Nitromethane | 2.0 hrs. | 65° C. | 22% | 18% |
| MEK | 3.25 hrs. | 65° C. | 8% | 2% |
| $CH_2Cl_2$ | 8.5 hrs. | 43° C. | 23% | 8% |
| EtOAc | 4.75 hrs. | 65° C. | 37% | 18% |
| THF | 4.0 hrs. | 67° C. | 15% | 3% |
| Toluene | 12 hrs. | 68° C. | 10% | 41% |

Different Lewis Acids were also substituted for zinc fluoride while maintaining a fixed reaction stoichiometry. All of these experiments were conducted in acetonitrile, the preferred reaction solvent. The data on the use of different promoters in the TMS ether glycosidic couplings are reported below in Table 2.

TABLE 2

GLYCOSIDIC REACTIONS WITH TMS-O-TIGOGENIN INFLUENCE OF LEWIS ACIDS
Reaction Stoichiometry:
α-Cellobiosyl Bromide Heptaacetate (1.0 Equivalent)
TMS-O-Tigogenin (1.0 Equivalent)
Lewis Acid (0.55 Equivalent)
$CH_3CN$

| | REACTION | | YIELD | |
|---|---|---|---|---|
| Lewis Acid | Time | Temp. | β-Glycoside | α-Glycoside |
| $ZnF_2$ | 3.0 hrs. | 65° C. | 72% | 4% |
| $Hg(CN)_2$ | 1.0 hr. | 65° C. | 7% | 0.2% |
| $Zn(CN)_2$ | 5.5 hrs. | 65° C. | 10% | 0.2% |
| $BF_3.Et_2O$ | 2.0 hrs. | 55° C. | Trace | — |
| $SnCl_4$ | 2.0 hrs. | 65° C. | 1% | 4% |
| $MgBr_2.Et_2O$ | 3.0 hrs. | 65° C. | 1% | 0.5% |
| TMS Triflate (0.1 Equiv.) | 20.0 hrs. | 65° C. | 2% | 3% |
| $ZnBr_2$ | 1.0 hr. | 65° C. | 3% | 10% |
| $MgF_2$ | 12.0 hrs. | 65° C. | 4% | 3% |
| $HgF_2$ | 1.0 hr. | 65° C. | 44% | 2% |

The zinc fluoride-mediated glycosidic coupling of TMS-O-tigogenin and α-cellobiosyl bromide heptaacetate was conducted in the presence of different acid catalysts for various reaction times. The results of these acid catalyzed reactions are summarized below in Table 3. This demonstrates that the reaction rate for the $ZnF_2$ TMS ether coupling can be accelerated by addition of small quantities of certain Lewis or mineral acids.

TABLE 3

$ZnF_2$-MEDIATED GLYCOSIDIC SYNTHESES USING TMS-O-TIGOGENIN INFLUENCE OF ACIDS & BASES
Reaction Stoichiometry:
α-Cellobiosyl Bromide Heptaacetate (1.0 Equivalent)
TMS-O-Tigogenin (1.0 Equivalent)
$CH_3CN$
$ZnF_2$ (0.55 Equivalent)
Acid/Base

| ACID OR BASE (EQUIVALENTS) | REACTION | | SOLVENT $CH_3CN$ | YIELDS | |
|---|---|---|---|---|---|
| | Time | Temp. | (Volume) | Beta-Glycoside | Alpha-Glycoside |
| HOAc(0.2) | 1.5 hrs. | 65° C. | 7.4 | 57% | 5% |
| HBr(0.2) | 0.5 hrs. | 65° C. | 7.4 | 54% | 3% |
| $BF_3.Et_2O(0.2)$ | 1.0 hr. | 65° C. | 7.4 | 53% | 4% |
| TEA(0.2) | 7.0 hrs. | 65° C. | 7.4 | 26% | 2% |

The zinc fluoride-mediated glycosidic coupling of TMS-O-tigogenin and α-cellobiosyl bromide heptaacetate was conducted in the presence of varying amounts of $ZnF_2$. The results of these zinc fluoride level evaluations are summarized below in Table 4. This demonstrates that high yields and selectivity are achieved using stoichiometric amounts of steroid and glycoside in the presence of reduced levels of metal salt promoters. Koenigs-Knorr glycoside couplings routinely use high levels (2–3 times) of metal salt promoters.

TABLE 4

GLYCOSIDIC COUPLING USING TMS-O-TIGOGENIN & $ZnF_2$ INFLUENCE OF ZINC FLUORIDE LEVELS

| EQUIVALENTS | | | REACTION | | SOLVENT $CH_3CN$ | ASSAYS YIELDS | |
|---|---|---|---|---|---|---|---|
| α-cellobiosyl bromide heptaacetate | TMS-O-Tigogenin | $ZnF_2$ | Time | Temp | Volume | Beta Glycoside | Alpha Glycoside |
| 1.0 | 1.0 | 1.5 | 1.0 hr. | 65° C. | 5.0 | 69% | 3% |
| 1.0 | 1.0 | 1.0 | 1.0 hr. | 65° C. | 5.0 | 71% | 4% |

TABLE 4-continued

GLYCOSIDIC COUPLING USING TMS-O-TIGOGENIN & $ZnF_2$
INFLUENCE OF ZINC FLUORIDE LEVELS

| EQUIVALENTS | | | | | SOLVENT | ASSAYS YIELDS | |
|---|---|---|---|---|---|---|---|
| α-cellobiosyl | | | REACTION | | $CH_3CN$ | Beta | Alpha |
| bromide heptaacetate | TMS-O-Tigogenin | $ZnF_2$ | Time | Temp | Volume | Glycoside | Glycoside |
| 1.0 | 1.0 | 0.5 | 2.5 hrs. | 65° C. | 5.0 | 71% | 4% |
| 1.0 | 1.0 | 0.25 | 11 hrs. | 65° C. | 7.4 | 26% | 3% |
| 1.0 | 1.0 | 0.25 | 23 hrs. | 65° C. | 7.4 | 9% | 25% |
| 1.0 | 1.0 | 0.1 | 22 hrs. | 65° C. | 7.4 | 6% | 6% |

This invention makes a significant advance in the field of steroidal glycosides by providing an efficient method of preparing peracyl tigogenin-, hecogenin-, 11-ketotigogenin-, diosgenin- or cholesterol-β-O-glycosides. The process provides excellent yields, excellent β-anomeric selectivity, reduced reaction by-products (e.g. peracyl glycosyl halide) and allows for a stoichiometric coupling while maintaining the yield and selectivity. The deacetylated end products are useful as anti-hypercholesterolemic agents.

It should be understood that the invention is not limited to the particular embodiments shown and described herein, but that various changes and modifications may be made without departing from the spirit and scope of this novel concept as defined by the following claims.

EXAMPLE 1

Preparation of Diosgenyl β-O-Galactoside Tetraacetate

To a 3-neck round bottom flask (250 ml) which was equipped with a mechanical stirrer, reflux condenser topped with a nitrogen inlet, and a thermometer, acetobromo-α-D-galactose (24.0 g, 58.4 mmol.), TMS-O-diosgenin (28.4 g, 58.4 mmol), zinc fluoride (3.32 g, 32.1 mmol) and 240 ml of acetonitrile were added. The mixture was heated to 60° C. under nitrogen. After 3.0 hours at 60° C., thin-layer chromatography (ethyl acetate/methylene chloride 1:1 eluant) showed that the reaction was complete. The mixture was cooled to room temperature and then dissolved in 220 ml of toluene. The toluene solution was washed with saturated sodium bicarbonate solution (100 ml), water (100 ml), saturated NaCl brine (20 ml), and finally dried over anhydrous magnesium sulfate. The mixture was filtered through Celite and then concentrated to an oil at reduced pressure. Eventually the oil crystallized upon further concentration. The crystals were triturated with ethanol (150 ml), filtered and dried in vacuo at 50°–55° C. to afford 31.51 grams of crude product.

The crude product (31.51 g) was suspended in 126 ml of toluene and then heated to about 110° C. for dissolution. The solution was slowly cooled to 80° C. and 158 ml of isopropanol was added. The resulting slurry was slowly cooled to 5°–10° C. and then granulated for 1 hour. The product was filtered and dried in vacuo at 50°–55° C. to afford 21.1 grams (49% overall yield) of a white crystalline product (m.p.=242.5°–244.0° C.) which was a chromatographically homogenous. $^1H$ and $^{13}C$ Nuclear Magnetic Resonance spectra were consistent with the product's structure.

EXAMPLE 2

"One Pot" Synthesis of Tigogenyl-β-O-Cellobioside Heptaacetate

β-Tigogenin (3.00 g, 7.20 mmol) and 50 ml of acetonitrile were added to a 100 ml, 3-neck round bottom flask which was equipped with a mechanical stirrer, thermometer, and distillation head. The slurry was heated to reflux (82° C.) under nitrogen and approximately 14 ml of distillate was removed overhead. A sample of the slurry was removed for a Karl Fischer water determination (K. F.=0.09%). The slurry was cooled to 70° C., and 1.08 ml of hexamethyldisilazane (5.12 mmol) was added. The white slurry was heated at 70° C. for 3.3 hours when thin-layer chromatography (EtOAc/Hexanes 1:1 eluant) showed that the silylation was complete. After the reaction mixture was cooled to 35° C., α-cellobiosyl bromide heptacetate (4.78 g, 6.84 mmol) and zinc fluoride (0.35 g, 3.42 mmol) were added. The thin slurry was reheated to 65° C. and then held at this temperature for 20 hours. Thin-layer chromatogram showed the complete disappearance of the cellobiosyl bromide and the formations of some β-glycoside.

The crude reaction mixture was quantitatively assayed by high pressure liquid chromatography which showed that the title β-glycoside was formed in 9.0% yield.

EXAMPLE 3

Tigogenyl β-O-Glucoside

α-D-Glucosyl bromide tetraacetate (24.0 g, 0.058 mole), trimethylsilyl-O-tigogenin (28.5 g, 0.058 mole), zinc fluoride (3.32 g, 0.032 mole) and acetonitrile (120 ml) were charged to a 250 ml 3-neck round bottom flask which was equipped with a condenser topped with a nitrogen inlet, mechanical stirrer, and thermometer. The reactants were heated to 60° C. under nitrogen with stirring, and then maintained at 60° C. for 2 hours when thin-layer chromatography indicated that the reaction was complete. The thin-slurry was cooled to 25° C. and 120 ml of methylene chloride was added to give a brownish colored solution. The solution was filtered, and the filtrate was washed with 5% $NaHCO_3$ solution (100 ml), water (100 ml), and finally a second water wash (100 ml). Some emulsions formed during the washes. The organic layer was dried over anhydrous magnesium sulfate (8 g) and then filtered through Celite. The solution was concentrated at reduced pressure to an oil and 600 ml of 2B ethanol was added. The mixture was heated to reflux and then slowly cooled to room temperature to crystallize the product. After granulating overnight, the glycoside was filtered, washed with 100 ml of ethanol, and then dried at reduced pressure for 4.5 hours at 45° C. Tigogenyl β-O-glucoside tetraacetate (24.1 g) was isolated in 55.4% overall yield. The physical and spectral properties of this material were identical to a reference standard.

Tigogenyl β-O-glucoside tetraacetate (22.0 g, 29.5 mmol) was added to 330 ml of absolute methanol containing 83 mg of potassium hydroxide. The slurry was heated to 50°–55° C. under nitrogen. After 3.5 hours at 50°–55° C., thin-layer chromatography ($CH_2Cl_2$/MeOH 4:1 eluant) showed that the deacetylation was complete and the slurry was cooled to 0°–5° C. The white product was filtered, washed with methanol, and then dried in vacuo at 40° C. overnight. Tigogenyl β-O-glucoside (16.5 g) was isolated in 96.8% yield from its tetraacetate. Analytical and spectral characterization data were consistent with the product's structure.

EXAMPLE 4

Preparation of Tigogenyl β-O-Cellobioside Heptaacetate

Trimethylsilyl-O-tigogenin (873.3 g, 1.79 mole), α-cellobiosyl bromide heptaacetate (1,250.0 g, 1.79 mole), zinc fluoride (101.6 g, 0.98 mole) and 6.25 liters of acetonitrile were charged to a 12-liter flask equipped with a mechanical stirrer, thermometer, and reflux condenser. The apparatus was purged with nitrogen and then maintained under a static nitrogen atmosphere. A sample of the heterogeneous reaction mixture was removed for a Karl Fischer determination (K. F.=0.04% $H_2O$). The reactants were then heated to 65±3° C. After 1.75 hours at 65° C., thin-layer chromatography showed that the reaction was essentially complete. The hazy brown solution was cooled to room temperature and 6.3 liters of methylene chloride were added. A one milliliter aliquot of the solution was removed for an hplc assay. A typical α/β anomeric ratio of 0.06 was obtained for the tigogenyl glycosides. The reaction mixture was filtered through Celite, and the filtercake was washed with 1 liter of $CH_2Cl_2$. The reaction filtrate and wash were combined. The $CH_2Cl_2$ solution was washed with water (4 liters), a 5% $NaHCO_3$ solution (4 liters), and finally dried over anhydrous magnesium sulfate (250 g). The $MgSO_4$ was filtered and washed with fresh $CH_2Cl_2$ (1 liter). The filtrate and wash were combined and concentrated to one-half volume (7.5 liters) by an atmospheric distillation. Seven liters of 2B-ethanol were added to the hot (65° C.) solution and the atmospheric strip was continued to remove an additional 6 liters of distillate. Additional ethanol (12 liters) was added and another 9 liters of distillate was removed before the white slurry was cooled to room temperature. The solids were granulated for 8 hours and then filtered. The product was washed with ethanol (500 ml) and then dried in vacuo at 45° C. overnight. Crude product (1,767.2 g) was obtained in a 95.5% weight yield. High-pressure liquid chromatography assay showed that the crude product contained 81.3% tigogenyl β-O-cellobioside heptaacetate and only 3.6% tigogenyl α-O-cellobioside heptaacetate. No β-cellobiosyl fluoride heptaacetate was detected.

If desired, the crude glycoside could be recrystallized from methylene chloride/ethanol to increase its potency. Although a recrystallization is not required before further processing.

By using a similar procedure to the above preparation, the following steroidal glycosides were synthesized from their trimethylsilyl sterols.

$ZnF_2$-Activated Glycosidic Couplings with TMS Ethers
Additional Examples

| Product | β-Glycoside Yield |
|---|---|
| Cholesteryl-β-O-Cellobioside Heptaacetate | 60% |
| Tigogenyl-β-O-Galactoside Tetraacetate | 58% |

EXAMPLE 5

Tigogenyl β-O-Cellobioside

Acetonitrile (700 ml) and zinc fluoride (6.10 g, 0.059 moles) were charged to 1-liter, 3-necked round bottom flask which was equipped with an overhead mechanical stirrer, thermometer, and distillation head. The mixture was heated to reflux (82° C.) and 105 ml of distillate was removed. The slurry was cooled to 30° C. and then a sample of the reaction mixture was removed for a Karl Fischer water determination (K. F.=0.023%). Trimethylsilyl-O-tigogenin (52.39 g, 0.107 moles) and α-cellobiosyl bromide heptaacetate (75.00 g, 0.107 moles) were added to the mixture, and then the slurry was heated to 65° C. under a nitrogen atmosphere. After the slurry was heated for 2.5 hours at 65° C., the mixture thinned to a tan hazy solution and thin-layer chromatograms using an ethyl acetate/hexanes (1:1) eluant indicated that the reaction was complete. The hazy solution was filtered through Celite and the filter cake was washed with 140 ml of acetonitrile. The acetonitrile wash and filtrate were combined, the total volume (840 ml) was measured, and a 1.0 ml sample was removed to determine assay yields of tigogenyl β-O-cellobioside heptaacetate (72%) and tigogenyl α-O-cellobioside heptaacetate (3%) by high pressure liquid chromatography.

The combined filtrate and wash were transferred to a 3-liter flask and the solution was heated to 50° C. under nitrogen. Absolute methanol (437 ml) was added over 15 minutes while maintaining the temperature at 50° C. Once the methanol addition was complete, 653 ml of deionized water was added over 1 hour. Tigogenyl β-O-cellobioside heptaacetate started to precipitate from solution after approximately 250–270 ml of water was added. The mixture was heated to reflux (73° C.) and then maintained at reflux for 2 hours while trimethylsilyl fluoride by-product (b.p.= 16° C.) was removed overhead. The slurry was cooled to room temperature (23° C.) and granulated overnight (15 hours). The β-glycoside was filtered and then washed with methanol (175 ml).

The β-glycoside, wet-cake was added to 700 ml of 2B-ethanol and then the slurry was heated to reflux (78° C.) to give a hazy solution. After 1 hour at reflux, the hazy solution was cooled to 22° C. and the precipitated product was granulated for 1 hour. The solids were filtered and washed with fresh ethanol (175 ml).

The ethanol wet-cake was transferred to a 1-liter round bottom flask equipped with a mechanical stirrer, thermometer, condenser, and nitrogen inlet. Methanol (620 ml) and a catalytic amount of sodium methoxide (0.21 grams) dissolved in 10 ml of methanol were added to the solvent-wet β-glycoside under nitrogen. The slurry was heated to reflux (66° C.) and then maintained at reflux for 2 hours. Thin-layer chromatography ($CH_2Cl_2$/methanol, 4:1) showed the complete deacetylation of the β-glycoside into tigogenyl β-O- cellobioside. The slurry was cooled to 22° C. and 110 ml of methanol was added to thin the mixture. An amorphous, white solid was filtered and washed with methanol (140 ml).

The wet-cake was resuspended in 980 ml of methanol and then stirred for 2 days at room temperature. Since microscopic examination of the slurry revealed the presence of amorphous and crystalline material, the slurry was filtered and the cake was washed with 200 ml of methanol. The above methanol reslurry procedure was repeated except that the slurry was heated to reflux (67° C.) for one hour and then cooled to room temperature. After the slurry stirred for 20 hours at room temperature, microscopic examination revealed the complete formation of the correct polymorph. The product was filtered, the cake washed with methanol (140 ml), and then dried in vacuo at 40° C. for 22 hours. Tigogenyl β-O-cellobioside (43.99 g) was obtained as a white solid in 55% overall yield from trimethysilyl-β-O-tigogenin. Chromatographic and physical properties of the product were identical to an authentic sample of tigogenyl β-O-cellobioside.

EXAMPLE 6

Preparation of Tigogenyl β-O-Cellobioside Heptaacetate Influence of Acids

An anhydrous hydrogen bromide solution was prepared by bubbling gaseous HBr (0.116 grams, 1.43 mmol) into 37 ml of acetonitrile. Zinc fluoride (0.407 g, 3.93 mmol), TMS-O-tigogenin (3.49 g, 7.15 mmol), and α-cellobiosyl bromide heptaacetate (5.00 g, 7.15 mmol) were then added to the hydrobromide solution under nitrogen. The mixture was sampled for a Karl Fischer water determination (K. F.=0.014% $H_2O$) and then heated to 65° C. After 0.5 hours at 65° C., the reaction was essentially complete as determined by thin-layer chromatography. The light yellow, thin slurry was cooled to about 24° C. and 37 ml of methylene chloride was added. After filtration, the volume of the reaction filtrate was measured and then analyzed by hplc as previously reported. The catalytic rate-accelerating effects of mineral and Lewis Acids and the rate-retarding effects of organic bases are reported in Table 3.

EXAMPLE 7

Preparation of Tigogenyl β-O-Cellobioside Heptaacetate Influence of Zinc Fluoride Levels Acetonitrile (5 ml), α-cellobiosyl bromide heptaacetate (1.00 g, 1.43 mmol), trimethylsilyl-β-O-tigogenin (0.70 g, 1.43 mmol), and anhydrous zinc fluoride (0.22 g, 2.15 mmol) were added to a 15 ml round bottom flask equipped with a magnetic stirrer, condenser, and thermometer. The mixture was heated to 65° C. and then monitored by tic using an ethyl acetate/hexanes (1:1) eluant for the disappearance of the TMS ether and α-cellobiosyl bromide heptaacetate. After 2.0 hours at 65° C., the reaction became a hazy solution and was essentially complete. The solution was cooled to ambient temperature, methylene chloride (5 ml) was added, and then the solution was filtered through Celite. The filter cake was washed with additional $CH_2Cl_2$ (10 ml). The wash and filtrate were combined and then quantitatively analyzed for β and α glycoside formation by using reference standards for refractive index detector response. Using 1.5 equivalents of zinc fluoride, tigogenyl β-O-cellobioside heptaacetate was produced in 69% yield. Product yields from TMS ether glycosidic couplings using different equivalents of $ZnF_2$ are reported in Table 4.

HPLC Chromatographic Conditions

Column: Water's Nova-Pak Silica 3.9×150 mm
Mobile Phase: Hexanes/Ethyl Acetate 3:2 (v/v)
Flow: 1 ml/minute
Injection: 50 ul
Detection: Refractometer
Precolumn: Silica
Retention Times: Tigogenyl β-O-cellobioside heptaacetate (3.74 minutes), Tigogenyl α-O-cellobioside heptaacetate (4.41 minutes)

EXAMPLE 8

11-Ketotigogenyl β-O-Cellobioside Heptaacetate

To an appropriately equipped 15 ml round bottom flask were added trimethylsilyl-β-O-11-ketotigogenin (0.67 g; 1.34 mmol), zinc fluoride (0.076 g; 0.74 mmol), α-cellobiosyl bromide heptaacetate (0.94 g; 1.34 mmol) and 7.2 ml of acetonitrile. The white slurry was purged with nitrogen and then heated to 65° C. After 2.2 hours at 65° C., thin-layer chromatography (toluene/acetic acid 8:3 eluant) showed the consumption of cellobiosyl bromide and the formation of the title product. The thin slurry was cooled to room temperature and 7 ml of methylene chloride was added to give a hazy solution. The solution was filtered through Celite and the filter cake was washed with fresh $CH_2Cl_2$ (5 ml). The combined filtrate and wash were extracted with water (8 ml), saturated sodium bicarbonate solution (8 ml), and water (8 ml), and then finally dried over anhydrous magnesium sulfate (1 gram). After filtration, the solution was concentrated at reduced pressure to give 1.40 grams of crude product.

The crude product was added to 29 ml of methanol and then heated to reflux (65° C.). Deionized water (9.6 ml) was slowly added to the refluxing solution. Once the addition was complete, the hazy solution was heated at reflux (72° C.)for an additional 20 minutes, cooled to room temperature, and the resulting slurry was granulated for 1 hour.

The white crystalline product was filtered and dried in vacuo at 40° C. overnight. The product was analyzed by $^1H$ NMR and compared to an authentic sample by high-pressure liquid chromatography to confirm its structure. 11-Ketotigogenyl-β-O-cellobioside heptaacetate was isolated (0.90 grams) in 64% overall yield.

EXAMPLE 9

Reaction of β-Cellobiosyl Fluoride Heptaacetate with Trimethylsilyl-β-O-Tigogenin Zinc fluoride (0.58 g; 5.61 mmol), trimethylsilyl-β-O-tigogenin (5.00 g; 10.2 mmol), and β-cellobiosyl fluoride heptaacetate (6.50 g; 10.2 mmol) were added to 45 ml of acetonitrile in a 3-neck, 125 ml round bottom flask. The mixture was stirred under nitrogen and then a sample of the slurry was removed for a Karl Fischer determination (K. F.=0.01% $H_2O$). A 30% hydrobromic acid solution (0.2 ml; 2.0 mmol) in glacial acetic acid was added and the resulting thin slurry was heated to 65° C. under nitrogen. After 24 hours at 65° C., a sample was removed for product analyses. Although the reaction was not complete as indicated by the presence of residual of starting materials, tigogenyl β-O-cellobiosyl heptaacetate was formed in 11% yield as determined by hplc analyses.

PREPARATIONS 1 and 2

Trimethylsilyl-β-O-11-Ketotigogenin and Trimethylsilyl Hecogenin

11-Ketotigogenin (0.93 g, 2.17 mmol) and triethylamine (0.49 g, 4.89 mmol) were added to 10 ml of acetonitrile at room temperature under nitrogen. Trimethylsilyl chloride (0.29 g, 4.34 mmol) was added to the slurry with a slight fuming and then the mixture was heated at 45° C. for 11 hours when thin-layer chromatography (ethyl acetate/-hexanes 3:2 eluant) showed that the silylation was complete. The slurry was cooled to 25° C., filtered, and the cake was washed with 10 ml of fresh acetonitrile. The product cake was dried overnight in vacuo at 40° C. and then reslurried in 13 ml of methanol to remove residual triethylammonium hydrochloride. After the solids were filtered, washed with methanol (10 ml) and dried at reduced pressure (35° C. for 17 hours), 0.69 grams of a white crystalline solid (m.p.=223°–226° C.) was isolated. The TMS ether of 11-ketotigogenin was obtained in 50% overall yield. Nuclear magnetic resonance ($^1$H and $^{13}$C), mass spectral, and combustion analyses were consistent with the product's structure.

The trimethylsilyl ether of hecogenin was also prepared by the trimethylsilyl chloride/TEA method. Trimethylsilylhecogenin (m.p.=252°–255° C.) was isolated in 57% overall yield.

PREPARATION 3

Trimethylsilyl-β-O-Tigogenin

To a 1-liter, 3-neck round bottom flask equipped with a mechanical stirrer, thermometer, and distillation head, β-tigogenin (75.0 g, 0.18 mole) was suspended in 0.66 liters of acetonitrile and the mixture was heated to reflux (84°–85° C.). Approximately 113 ml of distillate was removed overhead and then the slurry was cooled to 70° C. and sampled for a Karl Fischer water determination (K. F.=0.10%). Hexamethyldisilazane (30.4 ml; 23.2 g, 0.14 mole) was added and the mixture was heated to 70° C. Some thinning of the thick white slurry occurred during the reaction. After 3.75 hours, thin-layer chromatography (ethyl acetate/hexanes 1:1 eluant) showed that the reaction was complete. The slurry was slowly cooled to 5° C. and then granulated for 2 hours. The product was filtered, washed with 166 ml of fresh, cold acetonitrile, and then dried in vacuo at 40° C. for 16 hours.

Trimethylsilyl-β-O-tigogenin (83.8 g) was isolated as a white solid (m.p.=193°–196° C.) in 95% yield. Spectral data ($^1$H and $^{13}$C NMR and M.S.) and combustion analyses were consistent with the structure of the TMS ether. Additional trimethylsilyl ethers which were prepared from sterols using hexamethyldisilazare (HMDS) procedure are reported below.

Trimethylsilyl Ethers of Sterols (HMDS Procedure)

| TMS Ether | Melting Point | Yield |
|---|---|---|
| TMS-β-O-diosgenin | 176–178° C. | 97% |
| TMS-β-O-cholesterol | 128–131° C. | 95% |

We claim:

1. A process for the preparation of 1-O-steroidal peracyl-β-glycosides comprising:

reacting heptaacyl-D-cellobiosyl-1-halide, tetraacyl-D-glucosyl-1-halide or tetraacyl-D-galactosyl-1-halide wherein the halide is bromide, fluoride or chloride and the acyl is alkanoyl ($C_1$-$C_6$), benzoyl or toluoyl and a compound of the formula

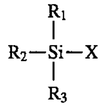

wherein $R_1$, $R_2$ and $R_3$ are each independently alkyl($C_1$-$C_6$), phenyl or phenyl alkyl($C_1$-$C_6$) and X is tigogen-3-O-yl, hecogen-3-O-yl, tigogen-11-keto-3-O-yl, diosgen-3-O-yl or cholester-3-O-yl in the presence of zinc fluoride under conditions capable of forming said 1-O-steroidal peracyl-β-glycosides.

2. The process as recited in claim 1 wherein the acyl is acetyl, $R_1$, $R_2$ and $R_3$ are each methyl, the peracyl glycosyl halide is the α-anomer and the reaction occurs in a non-protic reaction inert solvent.

3. The process as recited in claim 2 wherein X is tigogen-3-O-yl.

4. The process as recited in claim 2 wherein X is hecogen-3-O-yl.

5. The process as recited in claim 2 wherein X is tigogen-11-keto-3-O-yl.

6. The process as recited in claim 3, 4 or 5 wherein said reaction occurs at about 20° C. to about 100° C., about 0.5 to about 1.5 equivalents steroidal trimethyl silyl ether is used and about 0.1 to about 1.5 equivalents zinc fluoride is used.

7. The process as recited in claim 6 wherein the solvent is acetonitrile.

8. The process as recited in claim 7 wherein the reaction is catalyzed by reaction-liberated acids or optionally added Lewis or protonic acids.

9. The process as recited in claim 8 wherein the acid is hydrobromic acid or hydrofluoric acid.

10. The process as recited in claim 7 wherein the 1-O-steroidal peracyl-β-glycosides are precipitated from acetonitrile by the addition of about 25% to 75% water and the remainder alcohol.

* * * * *